US012788496B2

(12) United States Patent
Belkind Shafir et al.

(10) Patent No.: US 12,788,496 B2
(45) Date of Patent: Nov. 10, 2026

(54) DISPLAYING MARKS ON WALLS OF EAR-NOSE-THROAT (ENT) LUMENS FOR IMPROVING NAVIGATION OF ENT TOOLS

(71) Applicant: BIOSENSE WEBSTER (ISRAEL) LTD., Yokneam (IL)

(72) Inventors: Haya Michal Belkind Shafir, Pardes Hanna Karkur (IL); Lior Zaritzky, Yokneam Illit (IL); Fadi Ziad Salfiti, Shefa-'Amr (IL); Izar Nidal, Umm el Fahem (IL); Kobi Kofren, Haifa (IL); George Gusein, Akko (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 786 days.

(21) Appl. No.: 18/108,147

(22) Filed: Feb. 10, 2023

(65) Prior Publication Data

US 2023/0277250 A1 Sep. 7, 2023

Related U.S. Application Data

(60) Provisional application No. 63/316,131, filed on Mar. 3, 2022.

(51) Int. Cl.

*A61B 34/20* (2016.01)
*A61B 34/10* (2016.01)
*A61B 90/00* (2016.01)
*A61B 17/24* (2006.01)

(52) U.S. Cl.

CPC .............. *A61B 34/20* (2016.02); *A61B 34/10* (2016.02); *A61B 90/37* (2016.02); *A61B 17/24* (2013.01); *A61B 2034/107* (2016.02); *A61B 2034/2051* (2016.02); *A61B 2034/2065* (2016.02)

(58) Field of Classification Search

CPC .................. A61B 2034/107; A61B 2034/2065
See application file for complete search history.

(56) References Cited

U.S. PATENT DOCUMENTS

| | | | | |
|---|---|---|---|---|
| 8,290,228 | B2 | 10/2012 | Cohen | |
| 9,589,204 | B2 | 3/2017 | Gremse | |
| 9,770,216 | B2 * | 9/2017 | Brown | A61B 6/50 |
| 10,098,602 | B2 | 10/2018 | Lee | |
| 10,362,964 | B2 | 7/2019 | Jung | |
| 2006/0004286 | A1 * | 1/2006 | Chang | A61B 90/16 606/198 |
| 2007/0049839 | A1 | 3/2007 | Odry | |
| 2013/0197357 | A1 * | 8/2013 | Green | A61B 6/12 600/424 |
| 2024/0324870 | A1 * | 10/2024 | Wong | A61B 1/307 |

OTHER PUBLICATIONS

ValREc0 "How to Beat Night Flight: Spyro The Dragon" Published Nov. 21, 2018. <https://www.youtube.com/watch?v=KVsmYoSaUZ0>. 1 screenshot. (Year: 2018).*

International Search Report for corresponding PCT Appln. No. PCT/IB2020/051774 dated Jun. 7, 2023.

* cited by examiner

*Primary Examiner* — Angela M Hoffa

(74) *Attorney, Agent, or Firm* — FBT GIBBONS LLP

(57) ABSTRACT

A method includes receiving a target location for performing a procedure in an organ of a patient and a mapping of a lumen located along a path to the target location. Based on the target location and the mapping received, the method further includes producing an endoscopic view of at least the lumen and displaying in the endoscopic view, on at least a wall of the lumen, one or more marks indicative of a progress of the procedure.

20 Claims, 4 Drawing Sheets

DISPLAYING MARKS ON WALLS OF EAR-NOSE-THROAT (ENT) LUMENS FOR IMPROVING NAVIGATION OF ENT TOOLS

CROSS REFERENCE TO A RELATED APPLICATION

This application claims the benefit of U.S. Provisional Patent Application Ser. No. 63/316,131 entitled “Displaying marks on walls of Ear-Nose-Throat (ENT) lumens for improving navigation of ENT tools” that was filed on Mar. 3, 2022, the contents of which are incorporated by reference in its entirety.

FIELD OF THE DISCLOSURE

The present disclosure relates generally to visualization in minimally invasive medical procedures, and particularly to visualization techniques for improving the navigation of minimally invasive tools in Ear-Nose-Throat (ENT) organs.

BACKGROUND OF THE DISCLOSURE

Minimally invasive procedures, such as ear-nose-throat (ENT) procedures, require navigation of a medical instrument through a lumen in order to position the distal end of the instrument at a target location. In some cases, when navigating the instrument in the patient ENT system, the user (e.g., physician) may encounter various problems. For examples, (i) the anatomical structure of the ENT system has bifurcations and curvatures that require sharp turns and may result in orientation loss and navigation errors, moreover, the complexity of the ENT anatomy may cause orientation loss, e.g., between moving up and moving left along a branch of an ENT organ, (ii) a flexible instrument (e.g., catheter) may impinge on a bone or cartilage, and responsively, move opposite to the desired direction, (iii) variations in the inner diameter of cavities and lumens along the navigation path may also interfere with the navigation. These constraints require detailed planning of the path to the target location, and selection of an instrument having suitable properties, such as flexibility, diameter, and environmental durability. Thus, it is important to have improved imaging of the path to the target location.

The present disclosure will be more fully understood from the following detailed description of the examples thereof, taken together with the drawings in which:

DETAILED DESCRIPTION OF EXAMPLES

Overview

Figure 1:
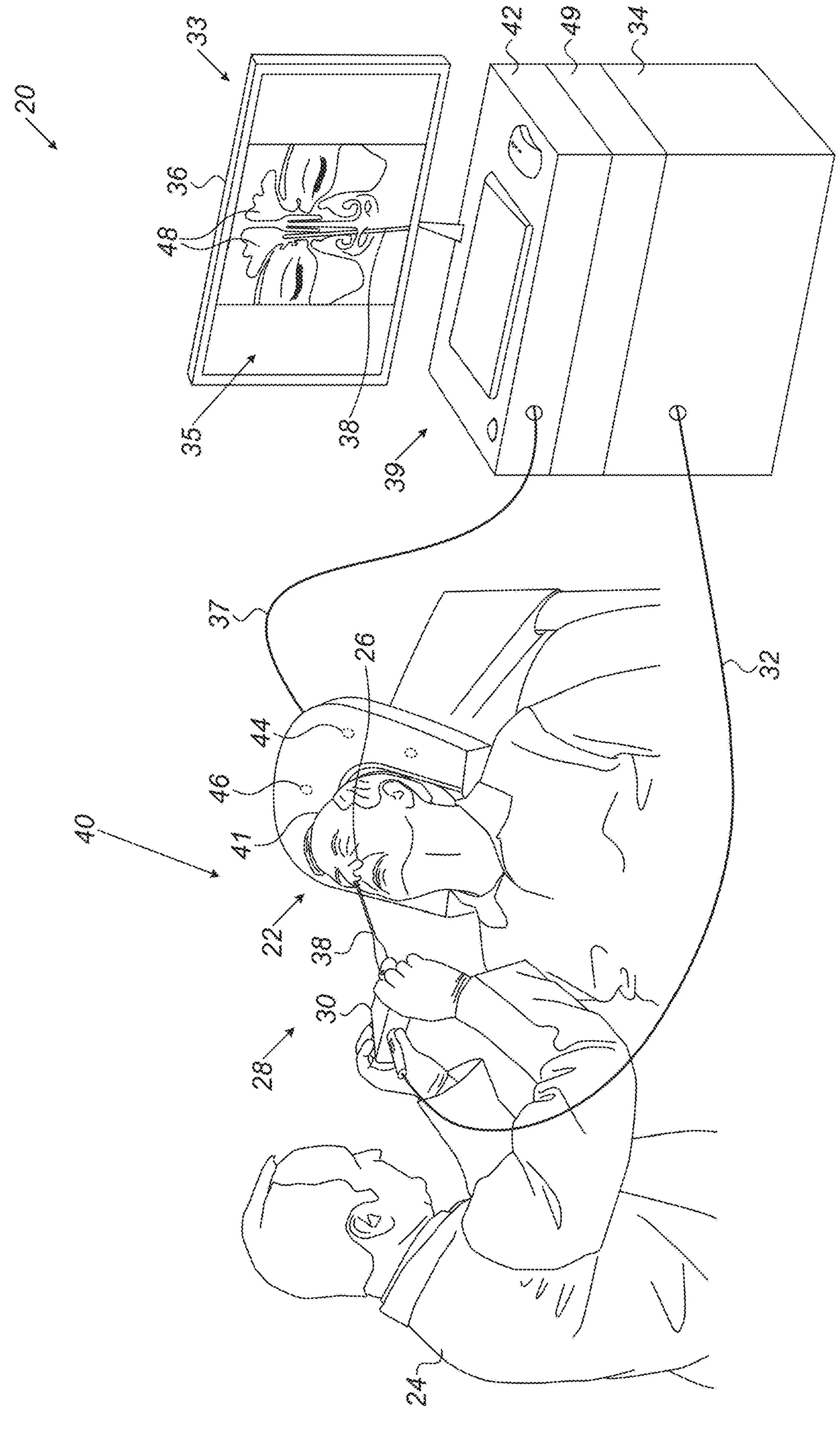
FIG. 1 is a schematic, pictorial illustration of an ear-nose-throat (ENT) procedure using an ENT treatment system, in accordance with an example of the present disclosure.

Examples of the present disclosure that are described hereinbelow provide techniques to enable improved imaging and navigation of a medical probe to a target location within an organ of a patient. In the present example, the organ comprises an ear-nose-throat (ENT) system, and the probe comprises an ENT tool, which is configured to perform a procedure in the ENT system. The ENT tool is sized and shaped for being comfortably inserted, e.g., through the nose, into a target location, e.g., a sinus of the patient. The ENT tool is also sized and shaped for allowing an additional medical instrument, such as a sinuplasty balloon, a surgical tool, a suction or irrigation tool, or any other suitable tool, to be fitted in a distal-end assembly (DEA) of the ENT tool, inserted through an anatomical lumen along the path into the sinus.

In some examples, a system for performing ENT procedures comprises one or more ENT tools, a memory and a processor. In some examples, when planning the ENT procedure, the memory is configured to receive and store a mapping of the ENT system. The mapping may comprise anatomical images from a medical imaging system such as a computerized tomography (CT), or any other suitable mapping of the patient ENT system. The memory is further configured to store the position of a target location, e.g., a sinus, for performing the medical procedure.

In some examples, the processor and/or the physician define a path for navigating the DEA of the ENT tool to the sinus in question. The path comprises a lumen, which is also mapped and stored in the memory.

In some examples, based on the mapping, the processor is configured to produce an endoscopic view of the lumen and other elements of the ENT system. The endoscopic view may be displayed from a point of view of the DEA of the probe or tool performing the procedure.

In some examples, the processor is configured to display, in the endoscopic view on at least a wall of the lumen (and typically on one or more other elements along the path and surrounding the path), one or more marks indicative of the progress of the procedure. For example, the marks may be indicative of the movement parameters of the DEA along the path toward, e.g., position and orientation of the DEA relative to the sinus in question.

In some examples, the processor is configured to display: (i) a first mark (e.g., a first color) over the position of the lumen and other ENT elements along the path, and (ii) a second, different color, over ENT elements that are positioned out of the path. In such examples, the physician has an indication of whether the DEA is positioned in the path or out of the path.

In some examples, the processor is configured to display one or more rings on one or more annular sections of the wall of the lumen. The rings are indicative of the direction of the path, and may also be indicative of the position and/or orientation of the DEA relative to the target location. In some examples, at least one of the rings may comprise a shimmering ring, which is moved along the path or shimmers at a specific location of the path.

In some examples, the processor is configured to display the rings moving along the path, and the movement speed of the rings may be indicative of the movement speed of the DEA along the path. In such examples, the physician has a real-time (RT) indication of ENT elements that the DEA is coming across (or passed threrethrough). Moreover, based on the movement speed of the rings, the physician may decide to move the DEA slower or faster along the path.

As described above, the ENT system has bifurcations and curvatures that require sharp turns and may result in orientation loss and navigation errors. In some examples, the processor is configured to display, at a given position and orientation of the DEA: (i) a visible section of the wall, which is visible in the endoscopic view, and (ii) an invisible section of the wall, which is invisible in the endoscopic view. In such examples, the processor is configured to display a given ring comprising: (i) a first section having a first transparency level, which is indicative of the visible section along the path, and (ii) a second section having a second transparency level, different from the first transparency level, which is indicative of the invisible section along the path. For example, when approaching a sharp turn, the processor is configured to display, in about 50% transparency level, "an invisible section of the ring", i.e., a section of the ring which is positioned on the invisible section of the path (e.g., located around the sharp turn). Similarly, the processor is configured to display a visible section of the ring (i.e., a ring section positioned on the visible section of the path) in about 10% transparency level (i.e., opaquer compared to that of the invisible section).

In some examples, the processor is configured to display, along the path, a line having one or more first axes, which are parallel with one or more second axes of the path, respectively. At each section of the lumen, the line is typically displayed along the respective first axis located at the center of the hollow lumen, i.e., at an equidistance from the walls defining the inner diameter of the lumen.

In some cases, during the navigation, the DEA is not moved along the center of the lumen. For example, the DEA is moved closer to one side of the wall. In some examples, the processor is configured to display an indication of the position of the DEA relative to the wall of the lumen. In such examples, the processor is configured to display (i) a first section having a first size along the path, which is indicative of a first distance of the DEA from the first section, and (ii) a second section having a second size along the path, which is indicative of a second distance of the DEA from the second section. Note that when the first size is different from the second size, the first distance is different from the second distance. In other words, when the DEA is closer to a given side of the wall, the ring section on the given side may appear wider compared to the section of the ring positioned on the opposite side of the wall.

In some examples, the processor is configured to display multiple rings at a different distance from one another. The inter-ring distance is indicative of the curvature level of the path. For example, before a sharp turn, the processor may display on the wall of the lumen, multiple rings arranged in close proximity to one another. This presentation provides the physician with an indication of approaching the sharp turn, so that the physician may move the DEA slower and navigate the DEA in accordance with the path of the sharp turn.

The disclosed techniques improve the planning and navigation of a medical probe in various branched organs, such as ENT, bronchoscopy, or neurology procedures.

System Description

FIG. 1 is a schematic, pictorial illustration of an ear-nose-throat (ENT) procedure using an ENT treatment system 20, in accordance with an example of the present disclosure. In some examples, ENT system 20 comprises a medical probe, referred to herein as an ENT tool 28, which is configured to carry out an ENT procedure, such as but not limited to treating infection from one or more sinuses 48 of a patient 22. In the context of the present disclosure, and in the claims, sinus 48 is also referred to herein as a target location.

In some examples, ENT tool 28 comprises a shaft 38, coupled to the distal end, which a physician 24 inserts into a nose 26 of patient 22. In the context of the present disclosure, and in the claims, the term distal end and distal-end assembly (DEA) are used interchangeably, and refer to components coupled to the distal tip of ENT tool 28. In some examples, ENT tool 28 further comprises a hand-held apparatus 30, coupled to a proximal end of shaft 38 and configured to assist physician 24 in maneuvering the distal end of shaft 38 in a head 41 of patient 22.

In an example, system 20 further comprises a magnetic position tracking system, which is configured to track the position of one or more position sensors in head 41. The magnetic position tracking system comprises magnetic field-generators 44 and multiple position sensors (not shown). The position sensors generate position signals in response to sensing external magnetic fields generated by field generators 44, thereby enabling a processor 34 (described in detail below) to estimate the position of each sensor as will be described below.

This method of position sensing is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1.

System 20 further comprises a location pad 40, which comprises field-generators 44 fixed on a frame 46. In the exemplary configuration shown in FIG. 1, pad 40 comprises five field-generators 44, but may alternatively comprise any other suitable number of generators 44. Pad 40 further comprises a pillow (not shown) placed under head 41 of patient 22, such that generators 44 are located at fixed, known positions external to head 41.

In some examples, system 20 comprises a console 33, which comprises a memory 49, and a driver circuit 42 configured to drive, via a cable 37, field-generators 44 with suitable signals so as to generate magnetic fields in a predefined working volume in space around head 41.

In some examples, console 33 comprises processor 34, typically a general-purpose computer, with suitable front end and interface circuits for receiving signals from tool 28 having multiple magnetic sensors (not shown) coupled thereto, via a cable 32, and for controlling other components of system 20 described herein.

In some examples, processor 34 is configured to estimate the position of each position sensor. Based on the estimated positions of the sensors, processor 34 is configured to derive the position, orientation and steering radius of curvature of the distal end of ENT tool 28 in the coordinate system of the magnetic position tracking system.

In the context of the present disclosure and in the claims, the terms "bending" "steering" are used interchangeably and refer to deflection of one or more sections of ENT tool 28.

In some examples, processor 34 is configured to receive via an interface (not shown), one or more anatomical images, such as computerized tomography (CT) images depicting respective segmented two-dimensional (2D) slices of head 41, obtained using an external CT system (not shown). The term "segmented" refers to displaying various types of tissues identified in each slice by measuring respective attenuation of the tissues in the CT system. In some examples, the CT images, and other sorts of images and mapping of the ENT of patient 22 are stored in memory 49. Moreover, memory 49 is configured to store the position of the target location, e.g., sinus 48, in any suitable coordinate system. For example, by registering between the coordinate systems of: (i) the CT images and mapping, and (ii) the position tracking system, both described above.

Console 33 further comprises input devices 39 for controlling the operation of the console, and a user display 36, which is configured to display the data (e.g., images and marks) received from processor 34 and/or to display inputs inserted by a user using input devices 39 (e.g., by physician 24).

In some examples, processor 34 is configured to select one or mode slices from among the CT images, such as an image 35, and to display the selected slice on display 36. In the example of FIG. 1, image 35 depicts a sectional front-view of one or more sinuses 48 of patient 22. Additional examples of the configuration of image 35 and various types of marks, are depicted in FIGS. 2, 3A, 3B, 4A and 4B below.

FIG. 1 shows only elements related to the disclosed techniques, for the sake of simplicity and clarity. System 20 typically comprises additional modules and elements that are not directly related to the disclosed techniques, and therefore, are intentionally omitted from FIG. 1 and from the corresponding description.

Processor 34 may be programmed in software to carry out the functions that are used by the system, and to store data in memory 49 to be processed or otherwise used by the software. The software may be downloaded to the processor in electronic form, over a network, for example, or it may be provided on non-transitory tangible media, such as optical, magnetic or electronic memory media. Alternatively, some or all of the functions of processor 34 may be carried out by dedicated or programmable digital hardware components.

Visualizing Path for Improving the Planning and Navigation of ENT Procedures

Figure 2:
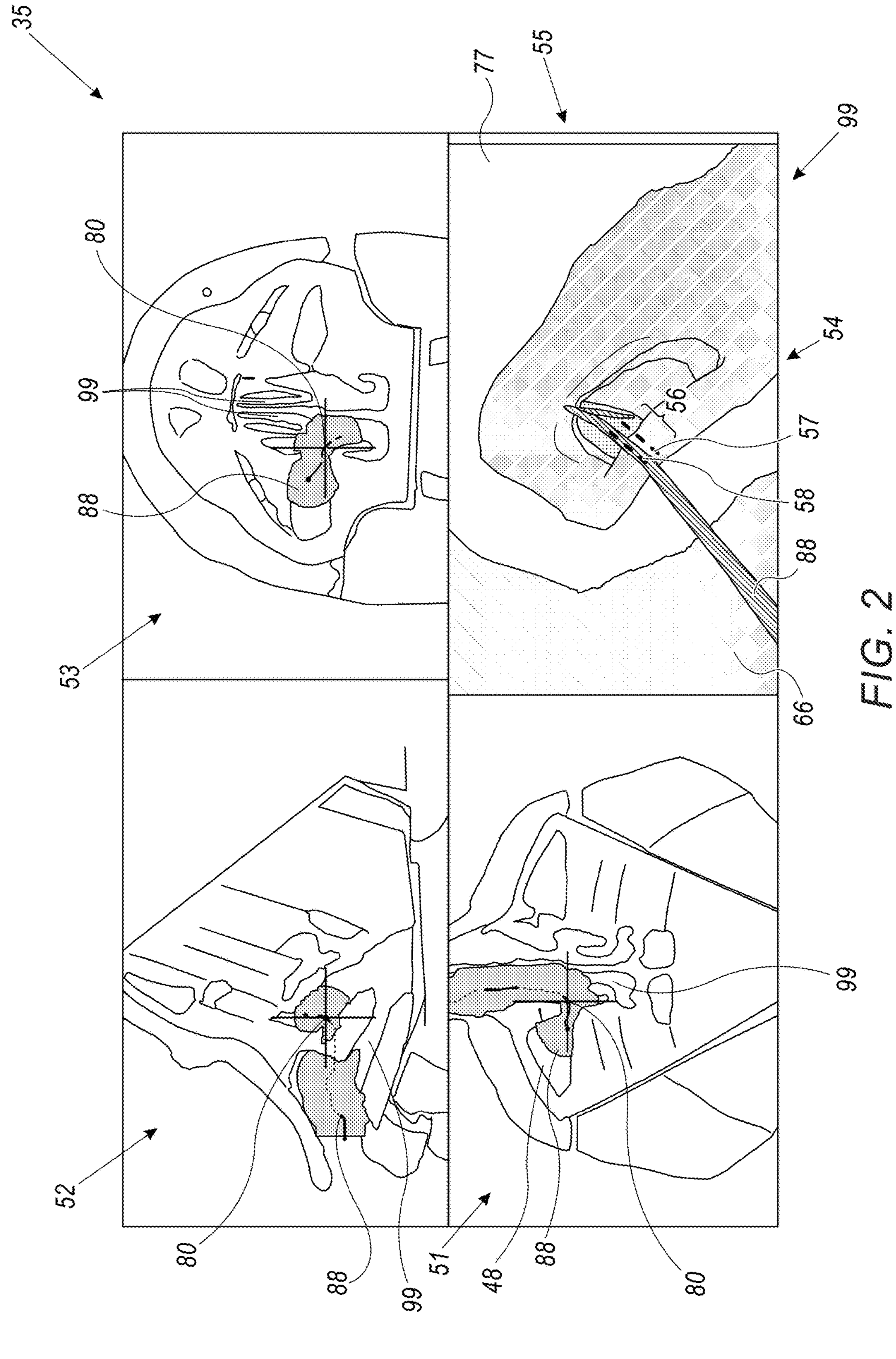
FIG. 2 is a schematic, pictorial illustration of an image of the patient ENT displayed to a user of an ENT system, in accordance with an example of the present disclosure.

FIG. 2 is a schematic, pictorial illustration of image 35 of ENT organs of patient 22 displayed to physician 24, in accordance with another example of the present disclosure.

In the example of FIG. 2, processor 34 is configured to display, e.g., on display 36, one or mode slices from among the CT images stored in memory 49, as described in FIG. 1 above. In the present example, an axial plane 51, a sagittal plane 52, and a coronal plane 53 of the ENT organs.

In some examples, processor 34 is configured to display a mark over the slices of the CT image. In the present example, the mark is indicative of a path 88 for moving the DEA of ENT tool 28 between a nostril of nose 26, and sinus 48, which is the target location for performing the treatment, as described in detail in FIG. 1 above.

In some examples, processor 34 is configured to display a position 80, which is indicative of the present position of the DEA within the ENT organs of patient 22.

In some examples, processor 34 is configured to display an endoscopic view 55 of cavities within the ENT organs of patient 22. In the context of the present disclosures, the ENT cavities are referred to herein as lumens 99 and sinuses 48. Moreover, endoscopic view 55 may be displayed from a point of view of the DEA of ENT tool 28, while being moved by physician 24 to perform the ENT procedure.

In some examples, the endoscopic view may be obtained using techniques known as virtual camera, which are known in the art.

Reference is now made to endoscopic view 55. In some examples, processor 34 is configured to display the endoscopic view based on: (i) the images and mapping stored in memory 49, and (ii) the position and orientation of the DEA received from the position tracking system described in FIG. 1 above. Endoscopic view 55 shows anatomical features of lumen 99 defined by a wall 66 of the lumen as will be described below.

In some examples, in endoscopic view 55, processor 34 is configured to display path 88 using a line disposed along the planned path between the nostril of nose 26 and sinus 48. In the example of endoscopic view 55, processor 34 is configured to display a section 54 of lumen 99 comprising multiple subsections, such as a subsection 56.

In some examples, processor 34 is configured to display the line indicative of path 88, such that within every subsection, the axes of lumen 99 and path 88 are parallel with one another. For example, in subsection 56, longitudinal axis 58 of path 88 is parallel with longitudinal axis 57 of lumen 99. Moreover, at each subsection, the longitudinal axis of the line indicative of path 88, may be located at the center of the hollow lumen, i.e., at an equidistance from the sides of wall 66 that define the inner diameter of lumen 99. In other examples, processor 34 is configured to display the line indicative of path 88 along the shortest route within path 88. Subsequently, processor 34 is configured to identify that the virtual line of path 88 is almost touching wall 66 of the lumen, and may redisplay the line (of path 88) farther from wall 66 but not necessarily at an equidistance from the sides of wall 66.

In some examples, processor 34 is configured to display on wall 66 one or more marks, such as a ring 77, which is described in detail in FIGS. 3A, 3B, 4A and 4B below.

Figure 3A:
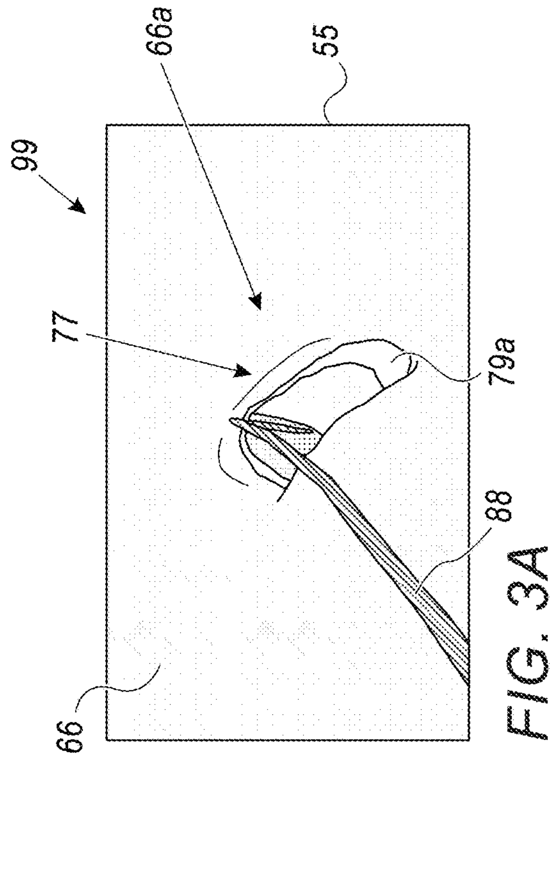
FIGS. 3A, 3B, 4A and 4B are schematic, pictorial illustrations of endoscopic views of marks displayed over a wall of an ENT lumen, in accordance with examples of the present disclosure.
Figure 3B:
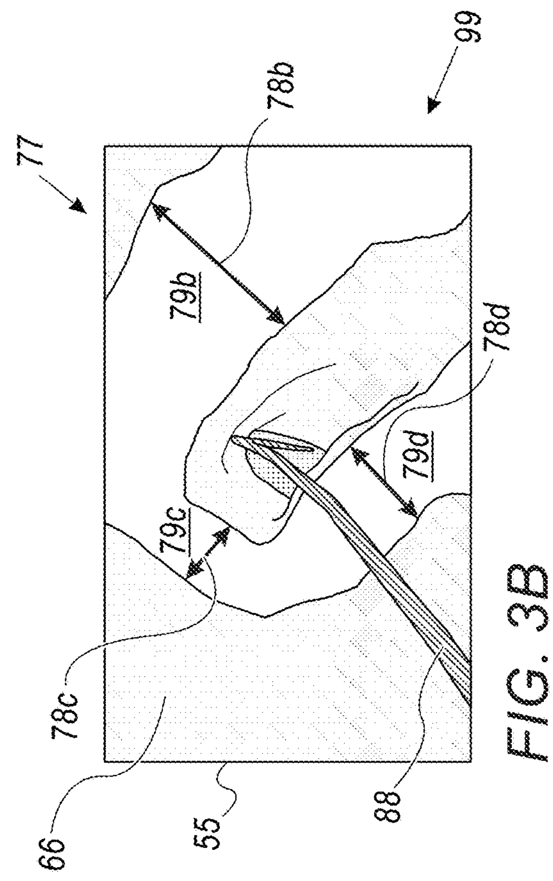

FIGS. 3A and 3B are schematic, pictorial illustrations of endoscopic views of rings 77 displayed over wall 66 in respective endoscopic views, in accordance with examples of the present disclosure.

Reference is now made to FIG. 3A. Typically, the anatomical structure of the ENT organs may comprise branched lumens 99 having bifurcations and curvatures that require sharp turns during the navigation of ENT tool 28. In some cases, after making a sharp turn of the DEA, physician 24 may lose orientation, which may result in navigation errors. In some examples, processor 34 is configured to display, at a given position and orientation of the DEA, a visible section 66*a* of wall 66, which is visible in the endoscopic view. Note that due to the curvature of the lumen 99 and path 88, an invisible section of the wall, which is invisible in the endoscopic view, is not presented. Moreover, in the example of FIG. 3A, processor 34 is configured to display only a section 79*a* or ring 77. Section 79*a* is positioned on visible section 66*a* of wall 66. By not displaying the hidden section of ring 77, processor 34 visualizes to physician 24 the curvature level of lumen 99. Moreover, the curvature level of lumen 99 is displayed by the curvature of the line indicative of path 88.

Reference is now made to FIG. 3B. In some cases, the anatomical structure of the ENT organs may dictate variations in the inner diameter and in the shape (of the cross section) of lumen 99. Such variations along path 88 may affect the navigation of the DEA of ENT tool 28 during the ENT procedure.

In the example of FIG. 3B, the variations in the diameter and shape (e.g., curvature and/or cross-sectional shape) of lumen 99 may result in ENT tool 28 being moved not along the center of the cross section of lumen 99. For example, the DEA of ENT tool 28 is moved closer to one side of wall 66. In some examples, processor 34 is configured to display an indication of the position of the DEA, relative to the sides of wall 66. In the example of FIG. 3B, processor 34 is configured to display different sections 79*b*, 79*c* and 79*d* of ring 77 having widths 78*b*, 78*c* and 78*d*, respectively. More specifically, width 78*b* of section 79*b* appears larger than widths 78*c* and 78*d* or sections 79*c* and 79*d*, respectively. In some examples, the different width is indicative of a different distance and/or orientation of the DEA relative to each section of ring 77. In other words, when the DEA of ENT tool 28 is closer to a given side of the wall, the ring section on the given side may appear wider compared to the section of the ring positioned on the different sides of the wall. Moreover, the width difference may be indicative of the orientation of the DEA while being moved along path 88 or lumen 99.

Figure 4A:
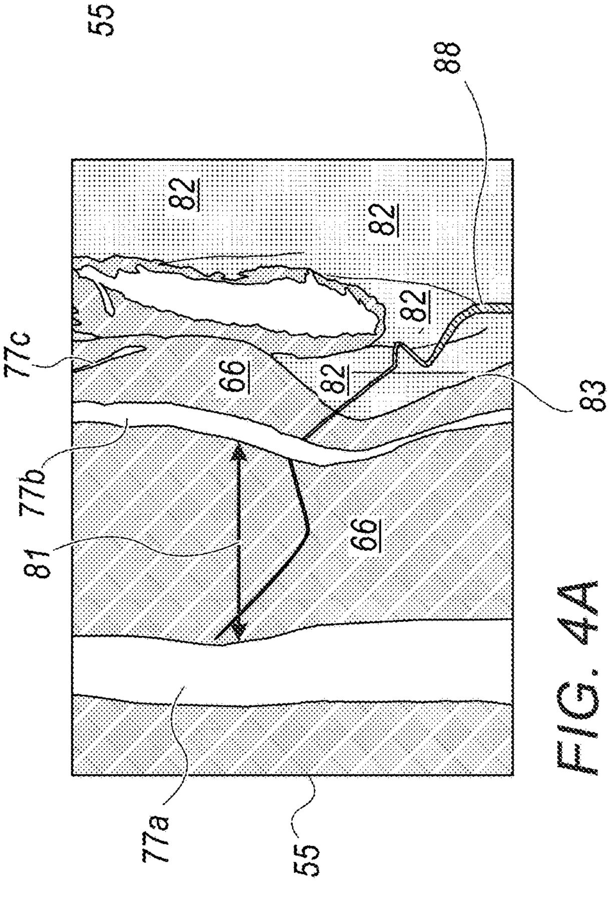
Figure 4B:
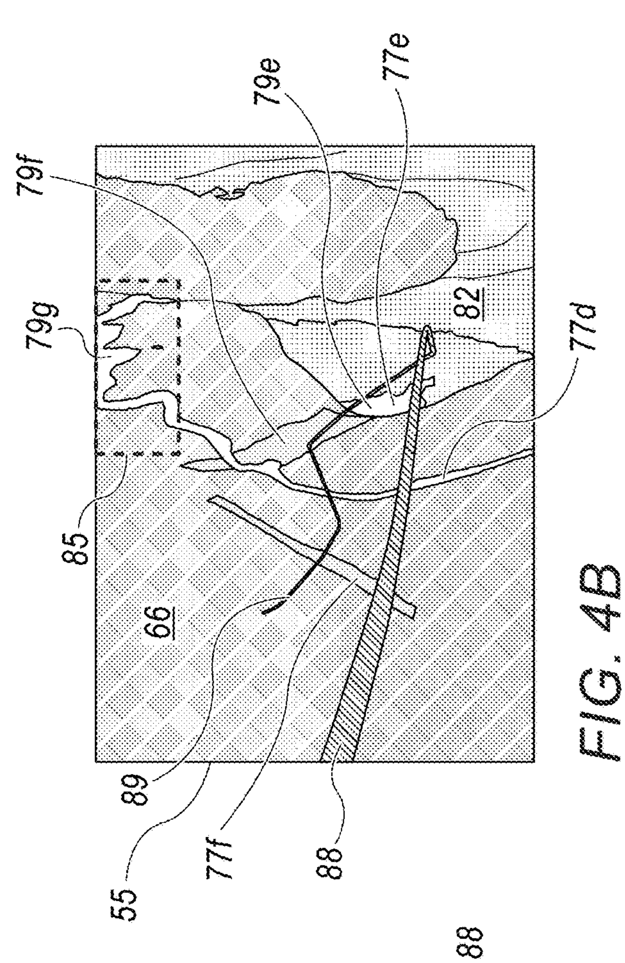

FIGS. 4A and 4B are schematic, pictorial illustrations of endoscopic views of rings 77 displayed over wall 66 of lumen 99, in accordance with other examples of the present disclosure.

Reference is now made to FIG. 4A. In some examples, processor 34 is configured to display multiple rings 77, in the present example shimmering rings 77*a*, 77*b* and 77*c*. In some examples, the high frequency of shimmering rings 77*a*, 77*b* and 77*c* on wall 66 is indicative of one or more sharp turns in path 88 (also shown by the multiple curvatures in the line of path 88). In other words, processor 34 is configured to produce a "drive safely" alert to physician 24 at "dangerous" sections of path 88. In such examples, a distance 81 between adjacent rings 77*a* and 77*b* is indicative of the "danger level" of the respective section of path 88.

In some examples, processor 34 is configured to visually differentiate between sections of the ENT organs that are along path 88 and sections that are out of lumen 99. For example, processor 34 is configured to display: (i) a first color on wall 66, and (ii) a second color, different from the first color, on sections of the ENT organs that are out of path 88. In the example of FIG. 4A, a brown color is assigned to wall 66, and an orange color is assigned to tissue 82 of sections 82 located out of lumen 99. The color selection must provide physician 24 with a distinguishable contrast between the different colors. For example, at an interface 83 the contrast between the colors of wall 66 and tissue 82 is distinguishable.

Additionally, or alternatively, processor 34 is configured to visually differentiate between wall 66 and tissue 82 using any other suitable marks, such as applying different partially transparent textures to wall 66 and tissue 82. The partially transparent textures allow physician 24 to see the morphology of wall 66 and tissue 82, and yet, to have a clear differentiation between first tissue located within lumen 99 and along path 88, and second tissue located out of lumen 99 and/or out of path 88.

Reference is now made to FIG. 4B. In some examples, processor 34 is configured to visually differentiate between rings 77 that, at a given position and orientation of the DEA, are positioned on sections that are visible or invisible in the endoscopic view. In the example of FIG. 4B, a ring 77*d* is displayed over a section of wall 66 that is visible in the endoscopic view (also referred to herein as a visible section), and a ring 77*f* is displayed over a section of wall 66 that is invisible in the endoscopic view (also referred to herein as an invisible section).

Moreover, a ring 77*e* has: (i) a section 79*e* displayed over a visible section of wall 66, and (ii) section 79*f* displayed over an invisible section of wall 66.

In some examples, processor 34 is configured to display, (i) ring 77*f* and (ii) section 79*f* of ring 77*e*, using higher transparency level (and/or different color or gray level) compared to that of ring 77*d* and section 79*e* of ring 77*e*. The difference in transparency level is indicative of the visibility of the respective sections of wall 66 in the endoscopic view shown in FIG. 4B. In other examples, the same technique may be applied to the color and/or transparency level of the line indicative of path 88. In the present example, a section 89 of the line of path 88 may have a different color and/or transparency level compared to that of the line of path 88, which is visible in the endoscopic view of FIG. 4B.

Additionally, or alternatively, processor 34 is configured to display at least one of rings 77, line of path 88, and sections thereof, using augmentation effects. For example, wall 66 appears on top of ring 77*f*, section 79*f* and section 89, whereas ring 77*d* and section 79*e* appear on top of wall 66.

In some cases, the morphology of the tissue(s) may alter along path 88, e.g., from having a smooth surface to having a rough surface. In some examples, when being moved along lumen 99, a physical contact may occur between the DEA and wall 66, which may cause damage to wall 66 and/or to the DEA. Therefore, it is important to visualize the morphology along path 88. In the example of FIG. 4B, the surface of a section 85 is rough compared to that of other sections of wall 66 shown in the endoscopic view. In some examples, processor 34 is configured to display a section 79*g* of ring 77*d*, such that the color contrast between sections 85 and 79*g* visualize the roughness level of wall 66 at section 85. Thus, when navigating ENT tool 28 in lumen 99, physician 24 may prevent any physical contact between the DEA and section 79*g*.

This particular configuration of marks displayed along walls 66 of lumen 99 are shown by way of example, in order to illustrate certain problems that are addressed by examples of the present disclosure, and to demonstrate the application of these examples in enhancing the performance of system 20. Examples of the present disclosure, however, are by no means limited to this specific sort of example marks, and the principles described herein may similarly be applied to other sorts of suitable marks, which may be displayed over other sorts of tissues and organs, and may be used for visualizing any suitable information in any sort of medical application and systems.

Figure 5:
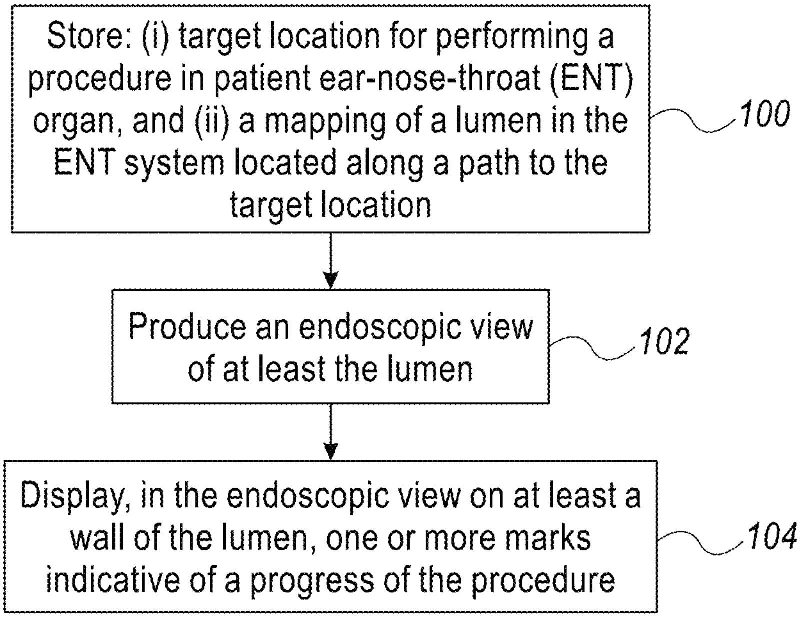
FIG. 5 is a flow chart that schematically illustrates a method for visualizing an ENT lumen to improve the planning and execution of ENT procedures, in accordance with an example of the present disclosure.

FIG. 5 is a flow chart that schematically illustrates a method for visualizing path 88 by displaying marks on wall 66 of lumen 99, so as to improve the planning and execution of ENT procedures, in accordance with an example of the present disclosure.

The method begins at a storage step 100, with memory 49 configured to store: (i) the position of sinus 48 and/or any other target location for performing a procedure in sinus 48 and/or any other ENT organ of patient 22, and (ii) a mapping of at least lumen 99, which is located along path 88 to the target location, as described in FIGS. 1 and 2 above.

At an endoscopic view production step 102, processor 34 produces endoscopic view 55 of at least lumen 99. For example, in FIGS. 2, 3A and 3B the endoscopic view comprises only lumen 99, and in FIGS. 4A and 4B, the endoscopic view comprises wall 66 of lumen 99, and tissue 82 that is typically located out of lumen 99.

At a displaying step 104 that concludes the method, processor 34 displays, in endoscopic view 55, on at least wall 66 of lumen 99, one or more marks, such as rings 77 that are indicative of the progress of the procedure. In some examples, the term "progress of the procedure" may comprise at least one of direction and/or speed of movement of the DEA of ENT tool 28 along path 88 and relative to the target location, as described, for example, in FIGS. 2 and 4A above.

In such examples, the marks are displayed, inter-alia, for assisting physician 24 in navigating ENT tool 28 along path 88. In an example, different colors and/or textures displayed over wall 66 and tissue 82, so as to visually differentiate between organs and/or tissues (e.g., lumen 99) along path 88 and organs and/or tissues (e.g., tissue 82) located out of path 88, as shown, for example, in FIG. 4A above. In another example, marks 77 and sections thereof are displayed over wall 66, and are indicative of sections that are visible and invisible in endoscopic view 55 at the present position and orientation of DEA, as shown, for example, in FIGS. 3A, 4A and 4B above. In yet another example, the size and shape of marks 77, and sections thereof, are indicative of the proximity between the DEA and wall 66, as described, for example, in FIG. 3B above.

In an example, the distance between adjacent rings 77 may be indicative of the curvature level of path 88 within a respective section of lumen 99, or at any other section along path 88. Such indications are assisting physician 24 in performing sharp turns along path 88, as described, for example, in FIG. 4A above. In another example, the shape of rings 77 and sections thereof, is indicative of the morphology of wall 66. For example, section 79*g* of ring 77*d* is indicative of increased surface roughness in section 85 of wall 66, as described in FIG. 4B above.

In some examples, in addition to endoscopic view 55 and the overlaid marks described above, processor 34 is configured to display: (i) in endoscopic view 55, the line indicative of path 88, and (ii) other imaging modalities of the ENT organs of interest, such as planes 51, 52 and 53, and path 88 and current position of the DEA displayed thereon, as shown in FIG. 2 above.

Although the examples described herein mainly address navigating of medical instruments in minimally invasive procedures carried out in the ear-nose-throat (ENT) of a patient, the methods and systems described herein can also be used in other applications. For example, the techniques of the present disclosure may be used, mutatis mutandis, for navigating a catheter in bronchoscopy or neurology procedures.

Example 1. A system (20) ring, comprises:

a memory (49), which is configured to store: (i) a target location (48) for performing a procedure in an organ of a patient (22), and (ii) a mapping of a lumen (99) located along a path (88) to the target location (48); and a processor (34), which is configured to: (i) produce an endoscopic view (55) of at least the lumen (99), and (ii) display, in the endoscopic view (55) on at least a wall (66) of the lumen (99), one or more marks indicative of a progress of the procedure.

Example 2. In regard to the system (20) of Example 1, the processor (34) may be configured to display: (i) a first mark indicative of a position in the path (88), and (ii) a second mark, different from the first mark, indicative of a position out of the path (88).

Example 3. In regard to the system (20) of Example 1 or Example 2, the processor (34) may be configured to display the endoscopic view (55) from a point of view of a distal-end assembly (DEA) of a probe (28) performing the procedure, and, to use the marks for displaying one or both of a position and an orientation of the DEA being navigated along the path (88) and relative to the target location (48).

Example 4. In regard to the system (20) of Example 3, the processor (34) may be configured to display, on one or more annular sections (54) of the wall (66) of the lumen (99), one or more rings (77), respectively, which are indicative of one or both of the position and the orientation of the DEA relative to the target location (48).

Example 5. In regard to the system (20) of Example 4, the processor (34) may be configured to move the rings (77) along the wall (66) of the lumen (99), and a first movement speed of the rings (77) may be indicative of a second movement speed of the DEA along the path (88).

Example 6. In regard to the system (20) of Example 4 or Example 5, the processor (34) may be configured to display the marks for displaying, at a given position and orientation of the DEA: (i) a visible section of the wall (66), which is visible in the endoscopic view (55), and (ii) an invisible section of the wall (66), which is invisible in the endoscopic view (55), and wherein the processor (34) is configured to display a given ring (77) comprising: (i) a first section having a first transparency level, which is indicative of the visible section along the path (88), and (ii) a second section having a second transparency level, different from the first transparency level, which is indicative of the invisible section along the path (88).

Example 7. In regard to the system (20) of any one of Example 4 to Example 6, at least one of the rings (77) may comprise: (i) a first section having a first size along the path (88), which is indicative of a first distance of the DEA from the first section, and (ii) a second section having a second size along the path (88), which is indicative of a second distance of the DEA from the second section, wherein when the first size is different from the second size, the first distance is different from the second distance.

Example 8. In regard to the system (20) of any one of Example 4 to Example 7, the processor (34) may be configured to display first and second rings (77) at a given distance from one another along the path (88), and the given distance may be indicative of a curvature level of the path (88).

Example 9. In regard to the system (20) of any one of Example 4 to Example 8, at least one of the rings (77) may comprises a shimmering ring (77*a*, 77*b* and 77*c*).

Example 10. In regard to the system (20) of any one of Example 1 to Example 9, the processor (34) may be configured to display, along the path (88), a line having one or more first axes, which are parallel with one or more second axes of the path (88), respectively.

Example 11. In regard to the system (20) of any one of Example 1 to Example 10, wherein the organ comprises an ear-nose-throat (ENT) system of the patient (22), wherein the target location (48) comprises a sinus of the ENT system, and wherein the procedure comprises one or both of sensing and treatment in the sinus.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art.

The invention claimed is:

1. A method, comprising:

receiving:

(i) a target location for performing a procedure in an organ of a patient, and (ii) a mapping of a lumen located along a path to the target location;

producing an endoscopic view of at least the lumen from a point of view of a distal-end assembly (DEA); and displaying in the endoscopic view, on one or more annular sections of a wall of the lumen that conform to a geometry of the lumen derived from the mapping, one or more rings indicative of a progress of the procedure;

wherein:

(i) a first section of at least one ring of the one or more rings is displayed at a first transparency level corresponding to a portion of the wall that is visible in the endoscopic view, and a second section of the at least one ring is displayed at a second, higher transparency level corresponding to a portion of the wall that is invisible in the endoscopic view, (ii) a width of a ring section of at least one ring of the one or more rings varies based on a distance between the DEA and a respective portion of the wall, and (iii) an inter-ring distance decreases at one or more sections of the lumen having increased curvature along the path.

2. The method according to claim 1, wherein displaying the one or more rings comprises displaying: (i) a first ring indicative of a position in the path, and (ii) a second ring, different from the first ring, indicative of a position out of the path, wherein the second ring is displayed on tissue outside the lumen and is visually differentiated from the wall of the lumen.

3. The method according to claim 2, further comprising visually differentiating the wall and the tissue outside the lumen by applying different partially transparent textures to the wall and to the tissue outside the lumen.

4. The method according to claim 1, wherein displaying the one or more rings comprises displaying one or both of a position and an orientation of the DEA being navigated along the path and relative to the target location.

5. The method according to claim 1, wherein displaying the one or more rings comprises changing, for at least one ring, a visual attribute distinct from transparency, width, and inter-ring distance to indicate an angular misalignment between an axis of the DEA and a local tangent of the path at a location of the at least one ring.

6. The method according to claim 5, wherein displaying the rings further comprises moving the rings along the wall of the lumen, and wherein a first movement speed of the rings is indicative of a second movement speed of the DEA along the path.

7. The method according to claim 1, further comprising, displaying along the path a line having one or more first axes, which are parallel with one or more second axes of the path, respectively.

8. The method according to claim 1, wherein the organ comprises an ear-nose-throat (ENT) system of the patient, wherein the target location comprises a sinus of the ENT system, and wherein the procedure comprises one or both of sensing and treatment in the sinus, and wherein the one or more rings displayed on the one or more annular sections of the lumen wall are computed from the mapping and calibrated to a pose of the DEA.

9. The method according to claim 1, wherein at least one of the one or more rings comprises a shimmering ring that is displayed at one or more sections of the lumen having increased curvature along the path to provide a visual alert to the user.

10. The method according to claim 1, further comprising detecting that an inter-ring distance falls below a predetermined threshold and, in response, changing a visual attribute of at least one ring of the one or more rings to indicate an elevated navigation caution level.

11. A system, comprising:

a memory, which is configured to store:

(i) a target location for performing a procedure in an organ of a patient, and (ii) a mapping of a lumen located along a path to the target location; and a processor, which is configured to:

(i) produce an endoscopic view of at least the lumen from a point of view of a distal-end assembly (DEA), (ii) display, in the endoscopic view, on one or more annular sections of a wall of the lumen that conform to a geometry of the lumen derived from the mapping, one or more rings indicative of a progress of the procedure, and (iii) detect that an inter-ring distance falls below a predetermined threshold and, in response, change a visual attribute of at least one ring to indicate an elevated navigation caution level; and wherein the processor is further configured to visually differentiate the wall and tissue outside the lumen by applying different partially transparent textures to the wall and to the tissue outside the lumen.

12. The system according to claim 11, wherein the processor is configured to display: (i) a first ring indicative of a position in the path, and (ii) a second ring, different from the first ring, indicative of a position out of the path, wherein the second ring is displayed on tissue outside the lumen and is visually differentiated from the wall.

13. The system according to claim 11, wherein the processor is configured to one or more rings for displaying one or both of a position and an orientation of the DEA being navigated along the path and relative to the target location.

14. The system according to claim 11, wherein the processor is configured to change, for at least one ring, a visual attribute distinct from transparency, width, and inter-ring distance to indicate an angular misalignment between an axis of the DEA and a local tangent of the path at a location of the ring.

15. The system according to claim 14, wherein the processor is configured to move the rings along the wall of the lumen, and wherein a first movement speed of the rings is indicative of a second movement speed of the DEA along the path.

16. The system according to claim 11, wherein the processor is configured to display, along the path, a line having one or more first axes, which are parallel with one or more second axes of the path, respectively.

17. The system according to claim 11, wherein the organ comprises an ear-nose-throat (ENT) system of the patient, wherein the target location comprises a sinus of the ENT system, and wherein the procedure comprises one or both of sensing and treatment in the sinus, and wherein the one or more rings displayed on one or more annular sections of the lumen wall are computed from the mapping and calibrated to a pose of the DEA.

18. The system according to claim 11, wherein at least one of the one or more rings comprises a shimmering ring that is displayed at one or more sections of the lumen having increased curvature along the path to provide a visual alert to the user.

19. The system according to claim 11, wherein at least one ring of the one or more rings comprises a shimmering ring that changes color at one or more sections of the lumen having increased curvature along the path to indicate a danger level of the respective section of the path.

20. A method, comprising:

receiving:

(i) a target location for performing a procedure in an organ of a patient, and (ii) a mapping of a lumen located along a path to the target location;

producing an endoscopic view of at least the lumen from a point of view of a distal-end assembly (DEA);

displaying in the endoscopic view, on one or more annular sections of a wall of the lumen that conform to a geometry of the lumen derived from the mapping, one or more shimmering rings, wherein a frequency of the shimmering rings on the wall is indicative of one or more sharp turns in the path; and visually differentiating the wall and tissue outside the lumen by displaying a first color on the wall and a second color, different from the first color, on the tissue outside the lumen, wherein a contrast between the first and second colors is distinguishable at an interface between the wall and the tissue.

* * * * *